United States Patent
Freund et al.

(10) Patent No.: US 7,628,759 B2
(45) Date of Patent: Dec. 8, 2009

(54) BLOOD PRESSURE MEASUREMENT DEVICE

(75) Inventors: Dirk Freund, Kelkheim (DE); Brigitte Harttmann, Niedernhausen (DE); Ulrich Heck, Krefeld (DE); Stefan Hollinger, Kronberg (DE); Gerrit Ronneberg, Darmstadt (DE); Fred Schnak, Kronberg (DE); Martin Simeth, Konigstein (DE); Dieter Wunder, Schotten (DE); Siegfried Zellermayer, Frankfurt (DE)

(73) Assignee: Kaz USA, Inc., Southborough, MA (US)

( * ) Notice: Subject to any disclaimer, the term of this patent is extended or adjusted under 35 U.S.C. 154(b) by 1119 days.

(21) Appl. No.: 10/999,631

(22) Filed: Nov. 30, 2004

(65) Prior Publication Data

US 2005/0131310 A1    Jun. 16, 2005

Related U.S. Application Data

(63) Continuation of application No. PCT/EP03/05628, filed on May 28, 2003.

(30) Foreign Application Priority Data

May 31, 2002    (DE) ................................ 102 24 042

(51) Int. Cl.
   *A61B 5/00*    (2006.01)
(52) U.S. Cl. ................... 600/490; 600/493; 600/499
(58) Field of Classification Search ................ None
   See application file for complete search history.

(56) References Cited

U.S. PATENT DOCUMENTS 4,206,765 A * 6/1980 Huber .................... 600/490
4,274,424 A * 6/1981 Kimura et al. .............. 600/499
4,429,699 A * 2/1984 Hatschek .................... 600/494
5,218,966 A * 6/1993 Yamasawa ................... 600/490
5,660,182 A    8/1997 Kuroshaki et al.
6,471,657 B2 * 10/2002 Sadritabrizi ................. 600/499
6,575,913 B1 * 6/2003 Woolley .................... 600/490
2002/0103440 A1    8/2002 Sadritabrizi

FOREIGN PATENT DOCUMENTS

| DE | 34 26 183 | 2/1986 |
| DE | 35 33 512 | 4/1987 |
| DE | 690 21 145 | 4/1996 |
| EP | 0 744 155 | 11/1996 |
| GB | 862875 | 3/1961 |
| GB | 2 348 134 | 9/2000 |
| WO | WO01/50952 | 7/2001 |

* cited by examiner

Primary Examiner—Robert L Nasser
(74) Attorney, Agent, or Firm—Darby & Darby (57) ABSTRACT

The invention relates to a blood pressure manometer comprising a housing, a cuff connected to the housing, a cuff storage element in which a section of the cuff can be retracted to adjust the width of the cuff, and a cuff tightener which pulls the cuff section into the cuff storage element with a predetermined tractive force. The cuff tightener comprises a pre-tensioned spring drive and a detachable withdrawal blocking element which prevents the cuff from withdrawing counter to the spring drive. The spring drive causes the cuff to automatically tighten with a pre-determined force, ensuring reproducible measuring results. The cuff storage element and the cuff tightener can be integrated into or engaged in a locking manner with the housing. An automatic switch-on mechanism switches the appliance on as soon as the cuff storage element is locked to the housing when the cuff is positioned on the limb.

43 Claims, 4 Drawing Sheets

BLOOD PRESSURE MEASUREMENT DEVICE

CROSS-REFERENCE TO RELATED APPLICATIONS

This is a continuation of PCT Application No. PCT/EP03/05628, filed on May 28, 2003, which claims priority to German Patent Application No. 102 24 042.6, filed on May 31, 2002, which is incorporated herein by reference in its entirety.

TECHNICAL FIELD

The present invention relates to a blood pressure measurement device with a device housing, in which device components such as a pressure gauge, a display unit and the like are accommodated, with a cuff which is connected to the housing and can be placed around a limb, with a cuff storage unit into which a cuff portion can be drawn in order to adjust the cuff width, and with a cuff tensioner which draws the cuff portion into the cuff storage unit with a predetermined tensile force.

BACKGROUND

In blood pressure measurement devices, it is customary to use a Velcro closure to tighten the cuff around a limb, in particular an upper arm or a wrist. To measure the arterial blood pressure, a pressure bladder provided in the cuff is pumped up until an artery is constricted. The fluid is then slowly released from the pressure bladder, whereupon the pulse causes an oscillation of the fluid pressure in the pressure bladder, and this can be used to determine, for example, the systolic and the diastolic blood pressure. However, variations or errors in the measurement values occur if the cuff is placed too tightly or too loosely around the limb. This cannot really be avoided, however, when applying the cuff by hand.

It has therefore already been proposed to tighten the cuff around the limb using a motor with a defined set-point tensioning force. DE 198 59 392 A1 discloses a tensioning device for the cuff of a blood pressure measurement device in which the tensioning force is automatically limited to a predetermined set-point tensioning force. An electric motor is used to drive two winding reels onto which the ends of the cuff are wound, and a sensor is used to determine and control the force with which the respective cuff portions are wound on and consequently with which the cuff is tensioned around the wrist. However, this known tensioning device for cuffs of blood pressure measurement devices is relatively expensive and requires its own sensor system in order to obtain the desired tensioning force. In addition, the cuff is awkward to apply and remove, because on each occasion the cuff has to be wound or unwound using the adjustment motor.

Further blood pressure measurement devices according to the prior art are already known from DE 34 26 183 A, GB 2 348 134 A, DE 35 33 513 A, U.S. Pat. No. 4,206,765 A, EP 0 744 155 A, WO 01/50952 A, US 2002/103440 A1, GB 862 875 A and U.S. Pat. No. 5,660,182 A. According to the prior art, in order to apply the cuff in the known blood pressure measurement devices, a loop is formed which is large enough to accommodate the limb to be received in it and which is then tightened. This procedure has proven awkward.

The object of the present invention is therefore to make available an improved blood pressure measurement device of the type mentioned at the outset, which avoids the disadvantages of the prior art and advantageously develops the latter. The aim is to ensure, preferably by simple means, that the cuff is tightened around the limb in a reproducible manner with a predetermined force, and that it is easy to apply and remove the cuff.

SUMMARY

According to an aspect of the invention, the cuff storage unit and the cuff tensioner are integrated in the device housing or can be brought into locking engagement with the device housing. In contrast to blood pressure measurement devices with motor-driven cuff tensioners which are arranged separately from the device housing on an opposite portion of the cuff, a substantially more compact arrangement can be achieved. In addition, the wearing comfort is improved, for example in long-term measurements, when the cuff is provided basically only on one circumferential portion with attachments, namely the device housing. It will be appreciated that the optionally releasable arrangement of the cuff storage unit and of the cuff tensioner on the device housing has particular advantages irrespective of the design of the drive of the cuff tensioner.

According to a possible embodiment of the invention, the cuff storage unit is part of the device housing, which in this case at the same time serves to receive the cuff portion which is to be drawn in. By means of this dual function of the device housing, an arrangement of particularly small size can be obtained.

In a development of the invention, however, the cuff storage unit is designed separately from the device housing. In particular, it can receive one end of the cuff and can be designed as a closure part which can be locked to the device housing, preferably which can be pushed into the device housing. In order to achieve a simple operation, a positive locking arrangement can be provided, particularly in the form of a snap-fit connection. The design of the cuff storage unit as a closure part combines the advantages of a compact structure with a high level of comfort upon application and removal of the cuff. After the cuff storage unit has been pushed into the device housing, these two components form a single unit. The unlocking and removal of the cuff storage unit from the device housing, however, permits complete opening of the cuff, so that the blood pressure measurement device can be easily released from the limb. It is not necessary to pull the cuff completely out of the cuff storage unit, for example in order to be able to slip the cuff off over the hand.

In order to achieve particularly easy handling, it is possible, in a development of the invention, to provide a common actuating lever for the locking of the cuff storage unit on the device housing and the pull-out catch. In order to open the cuff, said actuating lever need only be pushed or pulled, which then simultaneously releases the locking of the cuff storage unit on the device housing and the pull-out catch of the cuff tensioner. This allows convenient use with one hand.

According to a further advantageous aspect of the present invention, an automatic switch-on device is provided which automatically switches the blood pressure measurement device on after the cuff has been applied to a limb. In this case, the switch-on device can in principle operate as a function of various switch-on conditions, the device being switched on when these conditions are met. Thus, it would in principle be possible to detect the tensioning force of the cuff and, when a predetermined value is exceeded, to switch the device on. However, a simpler switch-on condition is preferably used. In particular, the automatic switch-on device can switch the device on when the cuff storage unit is brought into engagement with the device housing. To do this, a switch for switching the blood pressure measurement device on and off can be provided on the device housing, and the cuff storage unit and the cuff tensioner can have an actuating means which brings the switch into its switch-on position when the cuff is applied. It will be appreciated that the automatic switch-on device also brings particular advantages irrespective of the design of the drive of the cuff tensioner, especially ensuring entirely problem-free handling of the device even by inexpert users.

In order to prevent the blood pressure measurement device from being switched on when the cuff is closed but not placed around a limb, the actuating means can have an interrupter which interrupts the operation of the device depending on the position to which the cuff has been drawn into the cuff storage unit, in particular when the cuff has been drawn fully into the cuff storage unit. The interrupter can operate as a function of the layers wound onto the winding reel. The interrupter is preferably operative when a defined portion of the cuff has reached the winding reel. The actuating means is interrupted in particular when the wind-on cuff portion has been wound fully onto the winding reel.

The switch on the device housing can have two contacts which are closed by two mating contacts, provided on the cuff storage unit, when the cuff storage unit is secured on the device housing. An interrupter component is preferably provided on the cuff and interrupts the connection between the two mating contacts when the cuff is drawn into the position in which it is fully drawn into the cuff storage unit. Accordingly, the switch-on device automatically switches the blood pressure measurement device on only when, on the one hand, the cuff is closed, i.e. the cuff storage unit is locked on the device housing, and, on the other hand, when the cuff has been pulled out at least partially, as is always the case when the cuff is applied to a limb.

In a further development of the invention, the cuff tensioner therefore comprises a prestressed spring drive cooperating with a releasable pull-out catch which prevents the cuff from being unintentionally pulled out counter to the spring drive. The spring drive automatically tightens the cuff with at least one individually predetermined force, which guarantees individually reproducible measurement results. The spring drive in this case exerts a constant tensioning force along a certain length of drawing-in, so that the desired set-point tensioning force is obtained irrespective of the thickness of the particular limb. Alternatively, the tensioning force can be individually constant or determined only as a function of the length of drawing-in and the thickness of the limb. In this way too, individually reproducible measurement results are obtained. The pull-out catch then holds the cuff at the tightened length and prevents the cuff from being further tightened when the pressure bladder assigned to the cuff is inflated. In contrast to the previously proposed electric motors or pneumatic drives, the simple spring drive functions without external power and exclusively as a result of its provided prestressing and as a result of the inherent spring force in the spring drive by the respective pulling-out and release of the cuff. All non-electrical energy stores such as a rubber spring or gas spring are suitable as the spring drive. A current supply and corresponding batteries or accumulators are not needed. Likewise, it is possible to dispense with corresponding control of the tensioning force by sensors, force transducers, etc. On the other hand, however, the design of the cuff tensioner according to the invention permits easy and rapid removal of the cuff. To do this, the pull-out catch simply needs to be released, so that the cuff can be drawn counter to the spring tension or can be removed from the device housing. The pull-out catch can be formed as a ratchet, a locking hook, an electromagnetic catch, or as an inhibition provided by insertion of the cuff storage unit into the housing (the interaction of housing and cuff storage unit causes inhibition).

In a development of the invention, the cuff tensioner is designed as a winding reel which is driven by the spring drive. In principle, it would also be possible to provide a linear drive in order to draw the cuff portion into the cuff storage unit, but it is preferable to provide a rotary drive which has a winding reel onto which the cuff portion to be drawn in is wound. The winding reel forms a winding storage element which is distinguished by the small amount of space it requires and by the compact arrangement which can thus be obtained overall. The pull-out catch preferably acts directly on the winding reel. Provision could also be made for the pull-out catch to clamp or otherwise secure the cuff itself. However, the pull-out catch preferably prevents unintentional reversal of the winding reel. It can advantageously consist of a locking toothing connected to the winding reel, and of at least one associated locking pawl.

In order to obtain an arrangement of small size without further transmission stages, the spring drive can have a torsion spring which is arranged in the interior of the winding reel and which is received on a rotationally fixed winding reel shaft on which the winding reel is rotatably mounted.

These and further features will become evident not only from the claims but also from the description and the drawings, and the individual features can each be realized individually or together in the form of subsidiary combinations in an embodiment of the invention and in other fields. An illustrative embodiment of the invention is shown in the drawing and is explained in more detail below.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
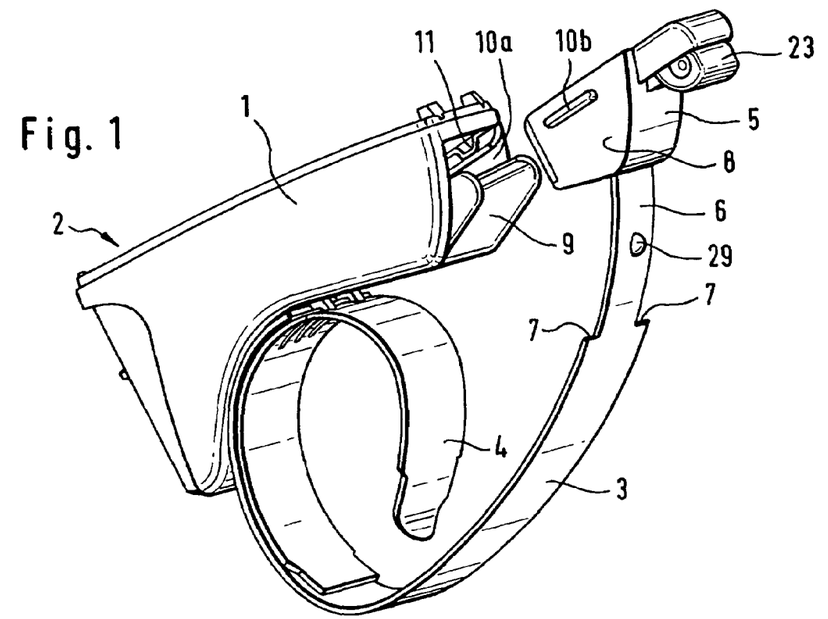
FIG. 1 shows a perspective view of an opened cuff of a blood pressure measurement device, which cuff is secured on the lower part of a device housing.

For reasons of clarity, a part of the device housing together with the components arranged in it has been omitted in FIG. 1. The figure only shows a lower part 1 of the device housing 2 on which a cuff 3 is secured, specifically by means of a support piece 4. In the device housing 2, it is possible to provide, in a manner known per se for wrist blood pressure measurement devices with measurement according to the oscillometric principle, and without these being specifically indicated, a pump for pumping up a pressure bladder assigned to the cuff 3, a pressure gauge, an evaluation unit and a display unit. The cuff 3 is secured on the lower part 1 by way of a fluid coupling, so that the pressure bladder (not shown in the figures) arranged in the cuff 3 can be inflated from the direction of the pump.

The free end of the cuff 3, that is to say the end not secured on the lower part 1, is received in a cuff storage unit 5 and can be drawn a distance into the latter. The cuff portion 6 which can be drawn into the cuff storage unit 5 is limited by a stop 7 which precisely defines a fully drawn-in position of the cuff 3. As FIG. 1 shows, the stop 7 can be formed by a step-shaped widening of the cuff 3 which, when the cuff portion 6 is drawn into the cuff storage unit 5, bears against the housing of the latter or against another suitable abutment piece. The cuff 3 therefore has an approximately U-shaped, flexible support piece 4, for example made of plastic, which, on the one hand, permits fastening of the cuff to the lower part 1 of the housing and, on the other hand, permits preliminary fixing of the blood pressure measurement device upon application to the limb or wrist. In addition, the cuff as usual has the pressure bladder which presses on the artery that is partially closed off for the measurement. Moreover, a textile band is provided in the cuff, one end of which textile band is fastened to the support piece, while the other end, the narrower end, can be wound up in the cuff storage unit 5. Textile band, support piece and pressure bladder are enclosed by a further textile material. In an advantageous variant, the outside of the textile material enclosure is designed integrally as a textile band that is narrower at an end area and can be wound up, so that an extra textile band part is dispensed with. The cuff is free from any possibilities of opening or separating, as are conventionally afforded by a touch-and-close fastener.

The cuff storage unit 5 has a housing part 8 or closure part 8 which can be pushed with an exact fit into a corresponding recess 9 provided for receiving the cuff storage unit in the lower part 1 of the device housing 2. As FIG. 1 shows, the recess 9 for receiving the cuff storage unit is arranged laterally on the lower part 1 so that the cuff storage unit 5 can be pushed in approximately in the circumferential direction. A push-in guide in the form of grooves 10a and matching projections 10b on the lower part 1 and the housing part 8 of the cuff storage unit 5 forces the two parts into a defined position in relation to one another.

Figure 2:
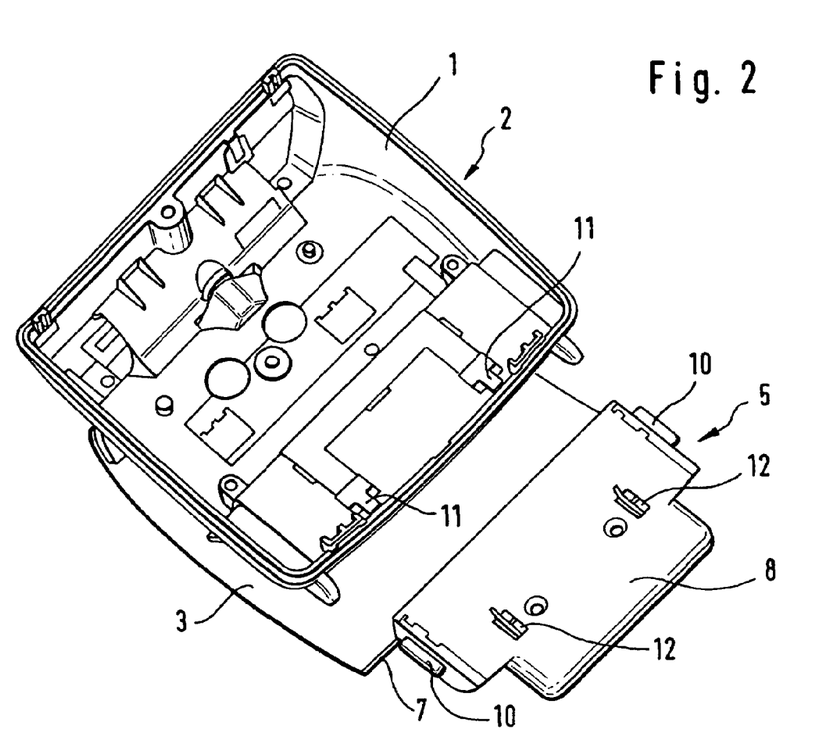
FIG. 2 shows a plan view of the lower part of the device housing and a cuff storage unit from FIG. 1 secured on the end of the cuff, which cuff storage unit can be pushed into the lower part of the device housing.

The cuff storage unit 5 and the lower part 1 of the device housing 2 can be locked to one another with a form fit. The corresponding locking device is in this case formed by two resilient locking hooks 11 which are provided in the recess 9 for receiving the cuff storage unit, and locking recesses 12 which cooperate with the locking hooks 11 and are arranged in the top face of the housing part 8 of the cuff storage unit 5 (see FIGS. 1 and 2). When the housing part 8 is pushed into the recess 9 for receiving the cuff storage unit, the locking hooks 11 are first pushed back. In the fully pushed-in position, the locking hooks 11 can spring back and snap into the locking recesses 12. The cuff storage unit 5 thus forms a closure part for the cuff 3, which closure part can be locked releasably on the device housing 2. This has the advantage that, when applying the device to the wrist, the cuff, with one end detached from the device housing 2, can be guided freely round the arm and can then be secured on the device housing 2. On the one hand, the cuff can thus be further opened and, on the other hand, the two parts to be connected to one another, namely the device housing or lower part 1 and the housing part 8, are of rigid design, so that none of these parts can yield flexibly upon connection.

Figure 3:
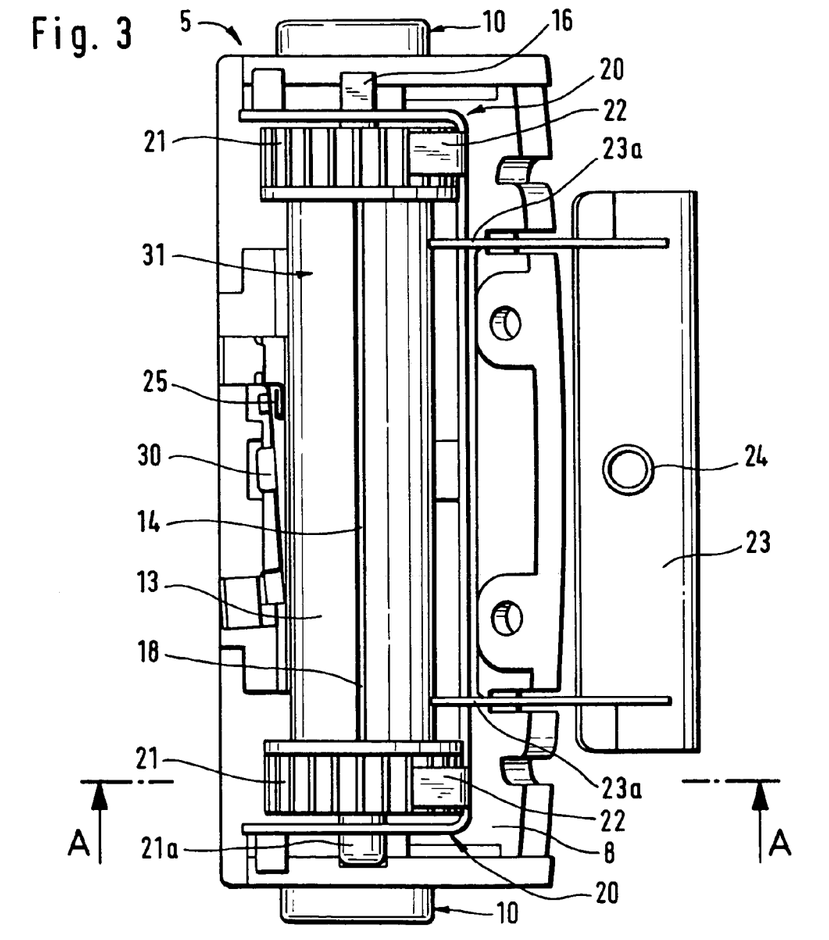
FIG. 3 shows a plan view of the winding reel of a cuff tensioner in the interior of the cuff storage unit from the previous figures.

Arranged in the interior of the housing part 8 of the cuff storage unit 5 there is a winding reel 13 on which the free end of the cuff 3 is secured and can be wound. To secure the cuff 3, the winding reel 13 can have a longitudinal slit 14 into which the end of the cuff 3 can be pushed. The winding reel 13 itself sits rotatably on a winding reel shaft 15, which is mounted in a rotationally fixed manner in the housing part 8. As FIG. 3 shows, the winding reel shaft 15 can sit in a rotationally fixed manner with flattened parts at the shaft ends arranged in corresponding recesses in the housing part 8 at one end. The flattened part 16 at the end of the winding reel shaft 15 can be seen in FIG. 5. At the other end, the pin 21a of the locking toothed wheel 21 sits in the corresponding recess of the housing part 8 as an abutment for the rotationally fixed connection opposite.

Figure 5:
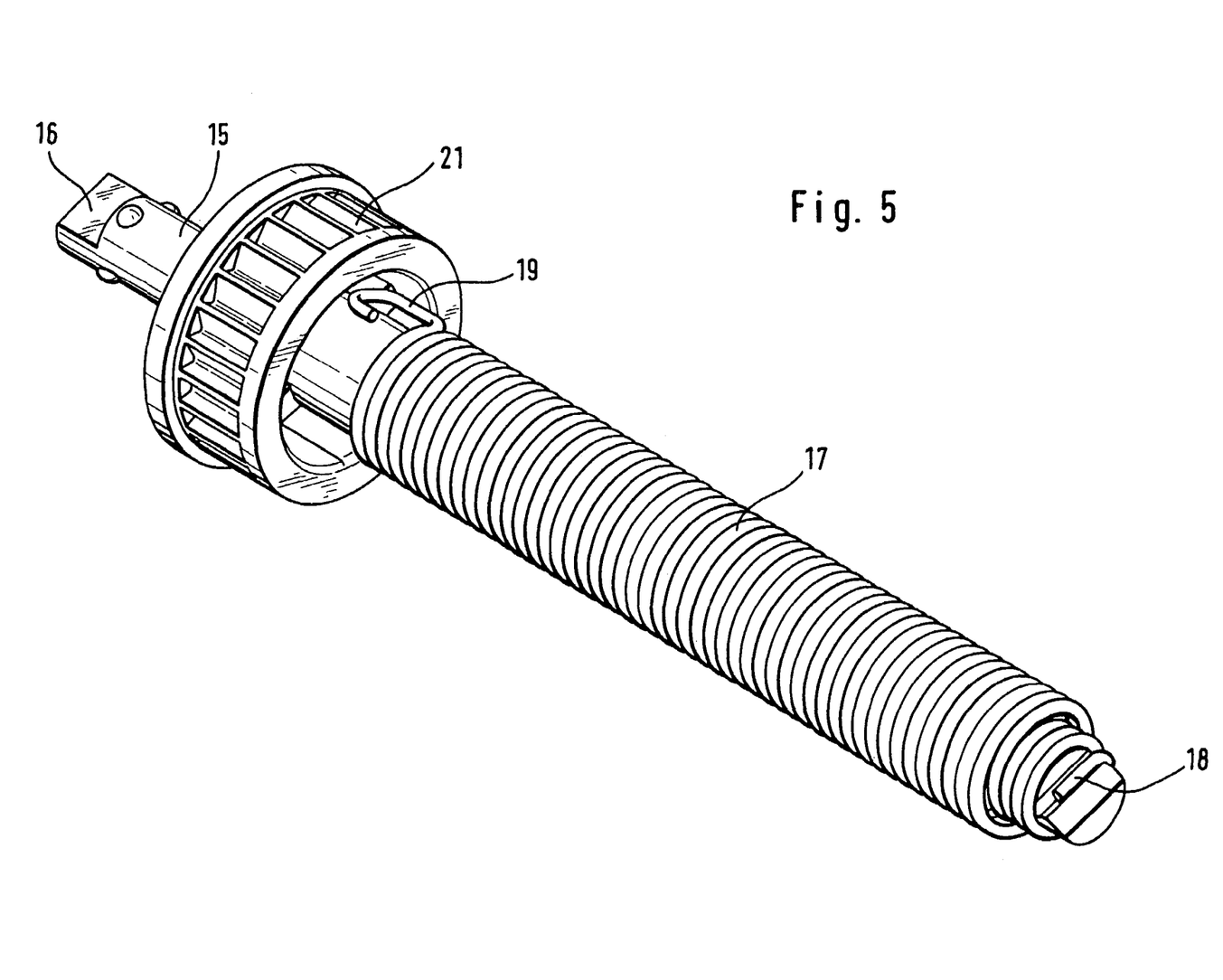
FIG. 5 shows a winding reel shaft with a torsion spring arranged on it for prestressing the winding reel from FIG. 3.

The winding reel 13 is prestressed in relation to the winding reel shaft 15, specifically by means of a torsion spring 17 which serves as a spring drive for the winding reel 13. As FIG. 5 shows, the torsion spring 17 sits with its helical windings on the winding reel shaft 15. A first spring end 18 is secured in a rotationally fixed manner on the winding reel shaft 15, while a second spring end 19 is secured in a rotationally fixed manner on the winding reel 13. By turning the winding reel shaft 15 while the winding reel 13 is at the same time held secure, the torsion spring 17 is prestressed. In this state, the winding reel 13 is fitted into the housing part 8 of the cuff storage unit 5, the flattened part 16 at the end of the winding reel shaft 15 being caught in the housing part 8 of the cuff storage unit 5. If the winding reel 13 is then released, the prestressed torsion spring 17 pulls the cuff 3, as far as the stop 7, into the housing part 8 of the cuff storage unit 5.

Figure 4:
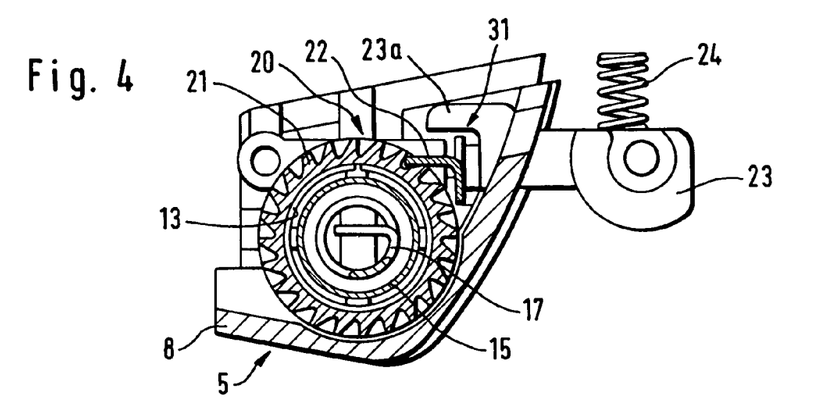
FIG. 4 shows a section through the cuff storage unit and the cuff tensioner along the line A-A in FIG. 3.

A pull-out catch 20 ensures that the cuff 3 is not pulled out unintentionally. As FIG. 3 shows, locking teeth 21 are provided at both ends of the winding reel 13 which form toothed sleeves and are connected to the winding reel 13 in a rotationally fixed manner. Locking pawls 22 provided on an actuating lever 23 engage in the locking teeth 21. As FIG. 4 shows, the actuating lever 23 is mounted pivotably about the axis 40 on the housing part 8 and is prestressed, by means of a spring arrangement 24, into its position in which it blocks the locking teeth 21, i.e. downwards according to FIG. 4. The prestressing of the actuating lever 23 on the one hand prevents rattling of the locking pawls 22 and on the other hand prevents unintentional release of the pull-out catch 20. As can be seen from FIG. 3, the pull-out catch is designed to allow free movement in the drawing-in direction. It blocks the winding reel 13 only in the pull-out direction. In FIGS. 3 and 4, the second abutment for the spring arrangement 24, namely the housing upper shell of the actuating lever, is not shown.

If the actuating lever 23 is pressed upwards counter to its spring prestressing according to FIG. 4, the locking pawls 22 are disengaged from the locking teeth 21, with the result that the cuff 3 can be pulled out from the cuff storage unit 5 by the torsion spring 17, counter to the spring prestressing.

In a preferred variant, the spring arrangement 24 is arranged pressing in the opposite direction, as explained above, so that the actuating lever 23 in FIG. 4 is prestressed upwards and the locking teeth 21 are unblocked. In this way, the actuating lever 23 is already pressed upwards by the spring prestressing, and the locking pawls 22 are disengaged from the locking teeth 21 so that the cuff 3 can be pulled out from the cuff storage unit 5 by the torsion spring 17, counter to the spring prestressing, and can be wound up with the prestressing of the torsion spring 17. Accordingly, in this variant, the cuff can be wound up and unwound independently of a pressing of the actuating lever 23. However, as is explained below, this applies only as long as the housing part 8 is also unlocked from the lower part 1, because then the spring prestressing of the locking hooks 11, which is greater than that of the spring arrangement 24 and acts counter to the latter in the locked state, does not provide for blocking of the cuff by means of the locking teeth 21.

The actuating lever 23 serves at the same time to release the lock between the cuff storage unit 5 and the device housing 2. As FIG. 4 shows, the actuating lever 23 has actuating portions 23a in the form of upwardly projecting bridges which lie directly under the locking recesses 12 in the housing part 8. If the actuating lever 23 according to FIG. 4 is pressed upwards, the actuating portions 23a press the locking hooks 11 in the recess 9 for the cuff out of the locking recesses 12 in the housing part 8 and prevent the locking hooks 11 from snapping into the locking recesses 12, so that the cuff storage unit 5 can be removed from the recess 9 for receiving the cuff storage unit. At the same time, the pull-out catch 20 is released, so that the cuff 3 can be pulled out from the cuff storage unit 5.

The locking hooks 11 are formed integrally on a U-shaped or H-shaped bent sheet metal part and are configured and arranged in such a way that, in the locked state, they protrude with a certain spring prestressing through openings into the cuff storage unit recess 9 into the locking recesses 12 of the housing part 8. The bent sheet metal part with the locking hooks 11 is secured on the lower part 1.

The following procedure can be used for applying and removing the cuff:

With the cuff opened, it is first placed on the wrist, the shell-shaped support piece 4 permitting rough preliminary positioning. The cuff 3 is then guided with its free end around the wrist. The actuating lever 23 is preferably pressed against the upper part of the housing 8 of the cuff storage unit 5 so that the pull-out catch 20 is released. In this way, the cuff storage unit 5 can be easily pushed into the recess 9 for receiving the cuff storage unit on the device housing 2. By releasing the actuating lever 23, the locking hooks 11 can snap into the locking recesses 12, so that the cuff is closed. At the same time, the torsion spring 17 tightens the cuff 3. By releasing the actuating lever 23, the pull-out catch 20 is also once again activated. Even, when inflating the cuff, the latter can no longer be pulled out from the cuff storage unit 5.

To release the cuff 3, all that needs to be done is to press the actuating lever 23 in order to unlock the pull-out catch 20 and move the locking hooks 11 out of the locking recesses 12, so that the cuff storage unit 5 can be removed from the device housing 2.

The preferred variant differs from the above procedure in that the actuating lever 23 only has to be pressed to unlock the locking hooks 11 from the locking recesses 12 so as to move the cuff storage unit 5 out of the device housing 2, but not in the other cases.

Figure 6:
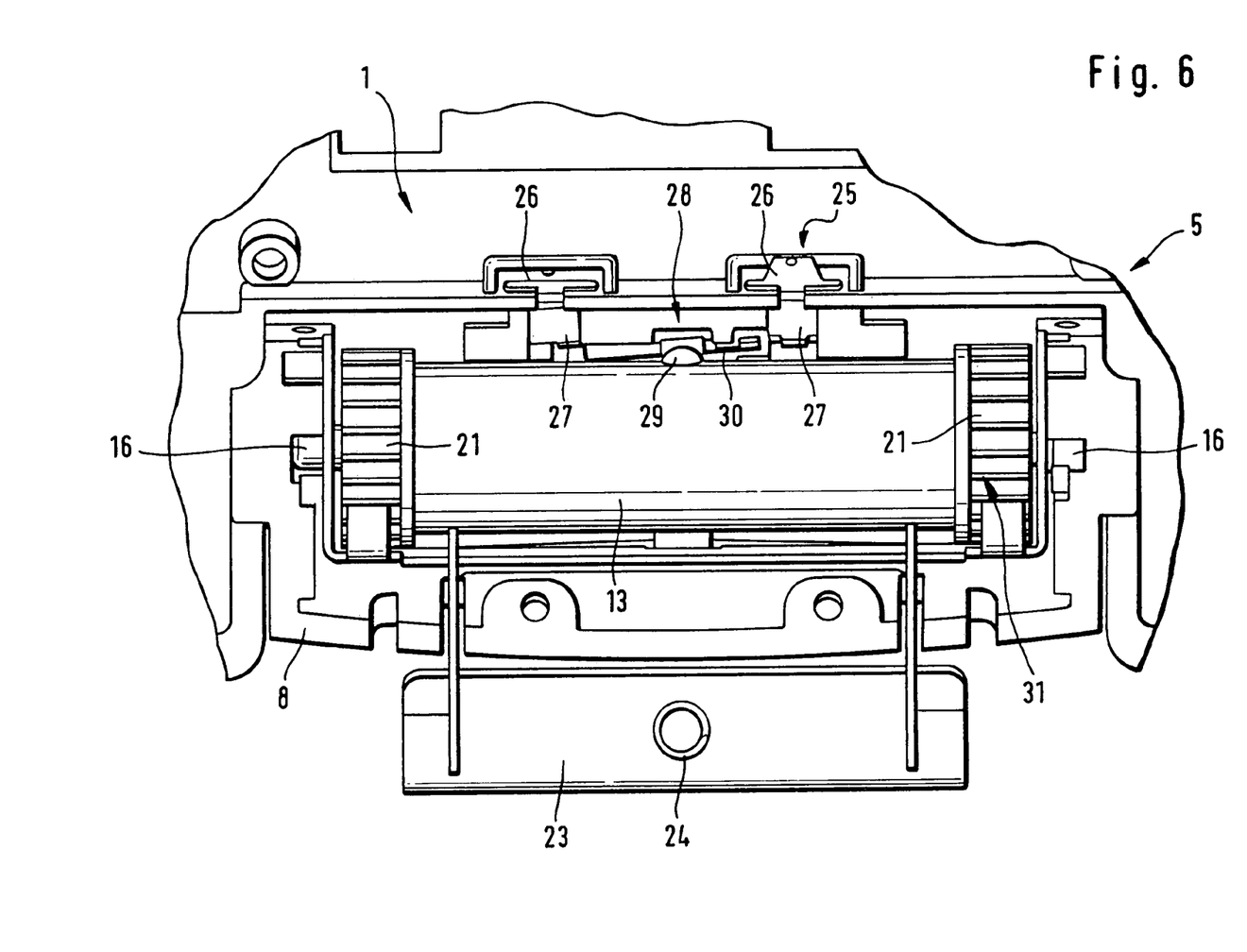
FIG. 6 shows a plan view of the interior of the cuff storage unit similar to FIG. 3, the cuff being shown in a fully drawn-in position in which an interrupter component provided on the cuff interrupts switch-on contacts.

The blood pressure measurement device advantageously has an automatic switch-on device 25. As is best shown by FIG. 6, two contacts 26 are provided in the recess 9 for receiving the cuff storage unit and they are electrically connected to the control means of the blood pressure measurement device in the device housing 2. Mating contacts 27 are provided on the housing part 8 of the cuff storage unit 5 and establish contact with the contacts 26 when the housing part 8 of the cuff storage unit 5 is pushed completely into the recess 9 for receiving the cuff storage unit. The contacts are expediently made suitably resilient. They can be arranged on the front end of the housing part 8, i.e. leading in the direction of insertion. The contacts 26 can be closed, i.e. connected, by the mating contacts 27, by which means the device is switched on.

However, in order to ensure that the device does not switch on when the cuff is closed but not placed around a limb, an interrupter 29 is provided which interrupts the closure of the contacts 26 or the connection of the mating contacts 27 as a function of the length of cuff wound onto the winding reel 13. As FIGS. 1 and 6 show, an interrupter component 29 in the form of a projecting knob, which can be designed as a rivet, is secured on the cuff 3. The interrupter component 29 is positioned on the cuff 3 in such a way that it comes to lie in the area of the mating contacts 27 when the cuff is in its fully drawn-in position. As FIG. 6 shows, the mating contacts 27 are connected to one another by a spring clip 30. When the cuff 3 is drawn fully into the cuff storage unit 5, the interrupter component 29 presses the spring clip 30 upwards, i.e. the mating contacts 27 disengage. As soon as the cuff 3 is pulled out a distance, the interrupter component 29 moves away from the spring clip 30, so that the mating contacts 27 are connected to one another. This ensures that the automatic switch-on device activates the device only when the cuff is actually placed around a limb.

Although not specifically shown, the winding reel can be assigned a width measurement means which determines the rolled-up length of the cuff, i.e. the cuff width and thus the circumference of the respective limb. The determination of the arm circumference via the rolled-up cuff can be included in the blood pressure calculation performed by the evaluation unit of the device, in order to further increase its accuracy and also to distinguish between different users.

The blood pressure measurement device is preferably designed in such a way that it can be arranged with the underside of the device housing 2 on the narrow side of the wrist. Accordingly, the display with its display functions is directed transversely with respect to the extent of the forearm, so that the display functions, such as blood pressure and/or inclination of the device, can be read off as soon as the device is placed with the forearm against the chest. The recess 9 for receiving the cuff storage unit is here oriented on the housing 2 with respect to the back of the hand. In one variant, it is oriented with respect to the palm of the hand.

A number of embodiments of the invention have been described. Nevertheless, it will be understood that various modifications may be made without departing from the spirit and scope of the invention. Accordingly, other embodiments are within the scope of the following claims.

What is claimed is:

1. A blood pressure measurement device comprising:
   a housing containing device components including a pressure gauge;
   a cuff connected to the housing and of a diameter selected to accommodate a human limb; and
   a cuff tensioner which draws a portion of the cuff into a cuff storage unit with a predetermined tensile force to adjust the cuff diameter with the cuff about a human limb;
   wherein the cuff storage unit and the cuff tensioner are releasably engageable with the housing and the cuff storage unit receives one end of the cuff and comprises a closure part which can be locked to the housing.

2. The blood pressure measurement device according to claim 1, wherein the housing defines a recess which receives the cuff storage unit for attachment of the closure part.

3. The blood pressure measurement device according to claim 2, wherein the closure part and the housing have corresponding push-in guides.

4. The blood pressure measurement device according to claim 1 further comprising an actuating lever operable to simultaneously release the cuff storage unit from the housing and release a pull-out catch of the cuff tensioner.

5. The blood pressure measurement device according to claim 1 further comprising a spring that releases a pull-out catch of the cuff tensioner when the cuff storage unit is unlocked from the housing.

6. The blood pressure measurement device according to claim 1 further comprising an activation switch responsive to insertion of the cuff storage unit into the housing.

7. The blood pressure measurement device according to claim 6, wherein the activation switch switches the blood pressure device off when the cuff storage device is removed from the housing.

8. The blood pressure measurement device according to claim 1, further comprising:
a switch for switching the blood pressure measurement device on and off, the switch being located on the housing; and
an interrupter which interrupts the operation of the device.

9. The blood pressure measurement device according to the claim 8, wherein the interrupter interrupts the operation of the device when the cuff has been drawn fully into the cuff storage unit.

10. The blood pressure measurement device according to claim 9, wherein, upon opening the cuff after completion of a measurement cycle, the measurement device continues to display measurement results.

11. The blood pressure measurement device according to claim 8, wherein the switch on the housing has two contacts closed by securing the cuff storage unit to the housing.

12. The blood pressure measurement device according to claim 11, wherein a connection between the two contacts is interrupted by the cuff, when the cuff is fully drawn into the cuff storage unit.

13. The blood pressure measurement device according to claim 1, wherein the cuff is free of touch fastener diameter adjustment.

14. The blood pressure measurement device according to claim 1 further comprising means for measuring the circumference of the limb on which the cuff is applied.

15. The blood pressure measurement device according to claim 14 wherein the measurement means are integrated into the cuff storage unit.

16. The blood pressure measurement device according to claim 1, wherein the cuff tensioner comprises a prestressed spring drive cooperating with a releasable pull-out catch which prevents the cuff from being pulled out counter to the spring drive.

17. The blood pressure measurement device according to claim 16, in which the cuff tensioner further comprises a winding reel which is arranged in the cuff storage unit and driven by the spring drive.

18. The blood pressure measurement device according to claim 17, wherein the pull-out catch consists of locking teeth connected to the winding reel, and at least one associated locking pawl.

19. The blood pressure measurement device according to claim 17, wherein the spring drive comprises a torsion spring arranged in the interior of the winding reel.

20. The blood pressure measurement device according to claim 19, wherein the winding reel sits on a rotationally fixed winding reel shaft on which the torsion spring is arranged.

21. The blood pressure measurement device according to claim 1 further comprising a display mounted on an outer surface of the housing.

22. A blood pressure measurement device comprising:
a housing;
a cuff connected to the housing and of a diameter selected to accommodate a human limb;
a cuff storage unit;
a cuff tensioner which draws a portion of the cuff into the cuff storage unit with a predetermined tensile force to adjust the cuff diameter with the cuff about a human limb; and
an activation switch operable to activate the blood pressure measurement device when the cuff is applied to a limb, wherein the cuff storage unit receives one end of the cuff and comprises a closure part which can be locked to the housing.

23. The blood pressure measurement device according to claim 22 wherein the cuff storage unit is integrated with the housing.

24. The blood pressure measurement device according to claim 22 further comprising a display mounted on an outer surface of the housing.

25. The blood pressure measurement device according to claim 22, wherein the housing defines a recess which receives the cuff storage unit for attachment of the closure part.

26. The blood pressure measurement device according to claim 25, wherein the closure part and the housing have corresponding push-in guides.

27. The blood pressure measurement device according to claim 22 wherein the cuff storage unit is releasably engageable with the housing.

28. The blood pressure measurement device according to claim 27 further comprising an actuating lever operable to simultaneously release the cuff storage unit from the housing and release a pull-out catch of the cuff tensioner.

29. The blood pressure measurement device according to claim 27 further comprising a spring that releases a pull-out catch of the cuff tensioner when the cuff storage unit is unlocked from the housing.

30. The blood pressure measurement device according to claim 27, wherein the activation switch switches the blood pressure device off when the cuff storage device is removed from the housing.

31. The blood pressure measurement device according to claim 30, wherein, upon opening the cuff after completion of a measurement cycle, the measurement device continues to display measurement results.

32. The blood pressure measurement device according to the claim 22, further comprising an interrupter which interrupts the operation of the device.

33. The blood pressure measurement device according to the claim 32, wherein the interrupter interrupts the operation of the device when the cuff has been drawn fully into the cuff storage unit.

34. The blood pressure measurement device according to claim 22, wherein a switch on the housing has two contacts closed by securing the cuff storage unit on the housing.

35. The blood pressure measurement device according to claim 34, wherein a connection between the two contacts is interrupted by the cuff, when the cuff is fully drawn into the cuff storage unit.

36. The blood pressure measurement device according to claim 22 wherein the cuff is free of touch fastener diameter adjustment elements.

37. The blood pressure measurement device according to claim 22 comprising means for measuring the circumference of the limb on which the cuff is applied.

38. The blood pressure measurement device according to claim 37 wherein the measurement means is integrated into the cuff storage unit.

39. The blood pressure measurement device according to claim 22, wherein the cuff tensioner comprises a prestressed spring drive cooperating with a releasable pull-out catch which prevents the cuff from being pulled out counter to the spring drive.

40. The blood pressure measurement device according to claim 39, in which the cuff tensioner further comprises a winding reel which is arranged in the cuff storage unit and driven by the spring drive.

41. The blood pressure measurement device according to claim 40, wherein the pull-out catch consists of locking teeth connected to the winding reel, and at least one associated locking pawl.

42. The blood pressure measurement device according to claim 40, wherein the spring drive comprises a torsion spring arranged in the interior of the winding reel.

43. The blood pressure measurement device according to claim 42, wherein the winding reel sits on a rotationally fixed winding reel shaft on which the torsion spring is arranged.

* * * * *